United States Patent [19]

Adams

[11] Patent Number: 5,583,904
[45] Date of Patent: Dec. 10, 1996

[54] CONTINUOUS LINEAR SCAN LAMINOGRAPHY SYSTEM AND METHOD

[75] Inventor: John A. Adams, Escondido, Calif.

[73] Assignee: Hewlett-Packard Co., Palo Alto, Calif.

[21] Appl. No.: 419,794

[22] Filed: Apr. 11, 1995

[51] Int. Cl.$^6$ ................................................. G01N 23/00
[52] U.S. Cl. .................... 378/22; 378/57; 378/62
[58] Field of Search .................... 378/17, 19, 21–27, 378/98.8, 62, 146, 57

[56] References Cited

U.S. PATENT DOCUMENTS

| | | |
|---|---|---|
| 2,292,859 | 8/1942 | Allibone . |
| 2,319,350 | 5/1943 | Schiebold . |
| 2,511,853 | 6/1950 | Kaiser . |
| 2,667,585 | 1/1954 | Gradstein . |
| 2,720,596 | 10/1955 | Acker . |
| 2,890,349 | 6/1959 | Huszar . |
| 2,998,518 | 8/1961 | Guntert . |
| 3,091,692 | 5/1963 | Verse . |
| 3,149,257 | 9/1964 | Wintermute . |
| 3,499,146 | 3/1970 | Richards . |
| 3,742,229 | 6/1973 | Smith et al. . |
| 3,780,291 | 12/1973 | Stein et al. . |
| 3,812,288 | 5/1974 | Walsh et al. . |
| 3,818,220 | 6/1974 | Richards . |
| 3,832,546 | 8/1974 | Morsell et al. . |
| 3,843,225 | 10/1974 | Kock et al. . |
| 3,894,234 | 7/1975 | Mauch et al. . |
| 3,928,769 | 12/1975 | Smith . |
| 3,962,579 | 6/1976 | Winnek . |
| 3,984,684 | 10/1976 | Winnek . |

(List continued on next page.)

FOREIGN PATENT DOCUMENTS

| | | | |
|---|---|---|---|
| 0139441 | 9/1983 | European Pat. Off. . | |
| 0225969 | 6/1987 | European Pat. Off. . | |
| 3028996 | 3/1982 | Germany | 378/26 |
| 62-67432 | 3/1987 | Japan . | |
| 62-116238 | 5/1987 | Japan . | |
| 868830 | 5/1961 | United Kingdom . | |

OTHER PUBLICATIONS

Hasenkamp, "Radiographic Laminography," *Materials Evaluation*, Aug. 1974, pp. 169–180.

Moler, "Development of a Continuous Scanning Laminograph," Final Report No. IITRI V6034–24, Oct. 1968.

Blanche, "Nondestructive Testing Techniques for Multilayer Printed Wiring Boards," Nondestructive Testing: Trends and Techniques, NASA SP–5082, Oct. 1968, pp. 1–13.

Hamre, "Nondestructive Testing Techniques for Muitilayer Printed Wiring Boards," Report No. IITRI–E6024–15, Sep. 1965.

Kruger et al., "Industrial Applications of Computed Tomography at Los Alamos Scientific Labratory," LA–8412–MS, Jun. 1980.

Stanley et al., "A New NDE Capability for Thin–Shelled Structures," AFWAL–TR–84–4120, Materials Lab, Wright Patterson AFB, Sep. 1984.

Deane et al., IRT Corp., "Using X-Ray Vision to Verify SMD-Board Quality," *Electronics Test*, Feb. 1987, pp. 32–35.

(List continued on next page.)

*Primary Examiner*—David P. Porta

[57] ABSTRACT

An improved laminography system that allows generation of high speed and high resolution X-ray laminographs by using a continuous scan method with two or more linear detectors and one or more collimated X-ray sources. Discrete X-ray images, with different viewing angles, are generated by each detector. The discrete X-ray images are then combined by a computer to generate laminographic images of different planes in the object under test, or analyzed in such a manner to derive useful data about the object under test. In one embodiment, the improved scanning laminography system does not require any motion of the source or detectors, but simply a coordinated linear motion of the object under test. Higher speed is achieved over conventional laminography systems due to the continuous nature of the scan, and due to the ability to generate any plane of data in the object under test without having to re image the object.

34 Claims, 6 Drawing Sheets

U.S. PATENT DOCUMENTS

| | | |
|---|---|---|
| 4,002,917 | 1/1977 | Mayo . |
| 4,007,375 | 2/1977 | Albert . |
| 4,032,785 | 6/1977 | Green et al. . |
| 4,075,489 | 2/1978 | Neal et al. . |
| 4,107,563 | 8/1978 | Oddell . |
| 4,130,759 | 12/1978 | Haimson . |
| 4,139,776 | 2/1979 | Hellstrom . |
| 4,147,933 | 4/1979 | Rougeot et al. . |
| 4,179,100 | 12/1979 | Sashin et al. ................... 378/19 X |
| 4,211,927 | 7/1980 | Hellstrom et al. . |
| 4,228,353 | 10/1980 | Johnson . |
| 4,234,792 | 11/1980 | DeCou et al. . |
| 4,260,898 | 4/1981 | Annis . |
| 4,287,425 | 9/1981 | Elliot, Jr. . |
| 4,340,816 | 7/1982 | Schott . |
| 4,349,740 | 9/1982 | Grassmann et al. . |
| 4,352,021 | 9/1982 | Boyd et al. . |
| 4,385,434 | 5/1983 | Zehnpfennig et al. . |
| 4,392,235 | 7/1983 | Houston . |
| 4,400,620 | 8/1983 | Blum . |
| 4,411,012 | 10/1983 | Pfeiler et al. ........................ 378/17 |
| 4,414,682 | 11/1983 | Annis et al. . |
| 4,415,980 | 11/1983 | Buchanan . |
| 4,426,722 | 1/1984 | Fujimura . |
| 4,472,824 | 9/1984 | Buckley . |
| 4,481,664 | 11/1984 | Linger et al. . |
| 4,491,956 | 1/1985 | Winnek . |
| 4,516,252 | 5/1985 | Linde et al. . |
| 4,521,902 | 6/1985 | Peugeot . |
| 4,561,104 | 12/1985 | Martin . |
| 4,575,751 | 3/1986 | Duschl . |
| 4,618,970 | 10/1986 | Rand et al. . |
| 4,628,531 | 12/1986 | Okamoto et al. . |
| 4,677,473 | 6/1987 | Okamoto et al. . |
| 4,688,241 | 8/1987 | Peugeot . |
| 4,688,939 | 8/1987 | Ray . |
| 4,718,075 | 1/1988 | Horn . |
| 4,720,633 | 1/1988 | Nelson . |
| 4,724,320 | 2/1988 | Ino et al. . |
| 4,730,350 | 3/1988 | Albert . |
| 4,731,855 | 3/1988 | Suda et al. . |
| 4,769,546 | 9/1988 | Kniffler et al. . |
| 4,803,639 | 2/1989 | Steele et al. . |
| 4,809,308 | 2/1989 | Adams et al. . |
| 4,852,131 | 7/1989 | Armistead . |
| 4,926,452 | 5/1990 | Baker et al. . |
| 4,955,045 | 9/1990 | Friede et al. . |
| 4,977,328 | 12/1990 | Van Vucht . |
| 5,012,498 | 4/1991 | Cuzin et al. . |
| 5,020,086 | 5/1991 | Peugeot . |
| 5,081,656 | 1/1992 | Baker et al. . |
| 5,097,492 | 3/1992 | Baker et al. . |
| 5,199,054 | 3/1993 | Adams et al. . |
| 5,259,012 | 11/1993 | Baker et al. . |
| 5,291,535 | 3/1994 | Baker et al. . |

OTHER PUBLICATIONS

Soron, IRT Corp., "X–Ray Inspection Meets Increased PWB Throughput", Density Challenge14 Part 1, *Electronics*, Oct. 1987, pp. 36–37.

Pound, "Image Processing Boosts the Power of Non–destructive Testing," *Electronic Packaging and Production*, Jun. 1985.

Casey, "X–Ray Inspection," *Manufacturing Systems*, Jul. 1987, p. 18ff.

Corey, IRT Corp., "Artificial Perception Gives Super Vision," *Research and Development*, Oct. 1984.

LaClair, "Nondestructive Measurement and Inspection Process," IBM Technical Disclosure Bulletin, vol. 18, No. 12, May 1976.

Hufault et al., "Lead–Indium Solder Joint Analysis," IBM Technical Disclosure Bulletin, vol. 19, No. 11, Apr. 1977.

Wittenberg, "IRT Improves SMT X–Ray Inspection System," *Electronic Engineering Times*, Oct. 5, 1987, p. 53.

Phelps, Christi, "Four Pi Captures Contact, Capital; Unveils Product," *San Diego Business Journal*, Week of Oct. 10–16, 1988.

Smith, Steven W. and Kruger, Robert A., "Fast Circular Tomography Device for Cardiac Imaging: Image Deflection Mechanism and Evaluation", *IEEE Transactions on Medical Imaging*, vol. MI–6, No. 2, Jun. 1987.

Four Pi Systems product brochure for "3 DX Series 2000 Automated Inspection System", Copyright 1988.

Juha, Mike, "Automated Inspection of Surface Mounted Device Solder Connections", *Proceedings of Soldering Technology Seminar—19–20 Feb. 1985*, Naval Weapons Center, China Lake, CA, Publication NWC TS 85–25, pp. 73–90.

Smith, Charles R. and Erker, Joseph W., "Low cost, high resolution x–ray detector system for digital radiography and computed tomography", *SPIE vol. 2009 X–Ray Detector Physics and Applications II*, 1993 pp. 31–35.

D. Meyer–Ebrecht and H. Weiss, "Tomosynthesis—3–D X–ray imaging by means of holography or electronics", *OPTICA ACTA*, vol. 24, No. 4, 1977, pp. 293–303.

Kolitsi et al., "A multiple projection method for digital tomosynthesis", *Med. Phys.*, vol. 19, No. 4, Jul./Aug. 1992, pp. 1045–1050.

Haaker et al., "Digital angiographic tomosynthesis with fewer artifacts", *Med. Phys.*, vol. 12, No. 4, Jul./Aug. 1985, pp. 431–436.

Kruger et al., "Reconstruction of blood vessels from x–ray subtraction projections: Limited angle geometry", *Med. Phys.*, vol. 14, No. 6, Nov./Dec. 1987, pp. 940–948.

Baranov et al., "System of Digital Tomosyntheis for Nondestructive Testing", *Plenum Publishing Corporation 0038–5492/88/2405*, 1989, pp. 321–327.

Vainberg et al., "Reconstruction of the Internal Three–Dimensional Structure of Objects Based on Real–Time Integral Projections", *Plenum Publishing Corporation 0038–5492/81/1706*, 1982, pp. 415–423.

CONTINUOUS LINEAR SCAN LAMINOGRAPHY SYSTEM AND METHOD

FIELD OF THE INVENTION

The invention relates to computerized laminography, and in particular, to systems which use a continuous linear scan method for high speed, high resolution inspection.

BACKGROUND OF THE INVENTION

Laminography techniques are widely used to produce cross sectional images of selected planes within objects. Conventional laminography requires a coordinated motion of any two of three main components comprising a laminography system, that is, a radiation source, an object being inspected, and a detector. The coordinated motion of the two components can be in any of a variety of patterns including but not limited to: linear, circular, elliptical or random patterns. Regardless of which pattern of coordinated motion is selected, the configuration of the source, object, and detector is such that any point in the object plane is always projected to the same point in the image plane and any point outside the object plane is projected to a plurality of points in the image plane during a cycle of the pattern motion. In this manner, a cross sectional image of the desired plane within the object is formed on the detector. The images of other planes within the object experience movement with respect to the detector thus creating a blur background on the detector upon which is superimposed the sharp cross sectional image of the desired focal plane within the object. Although any pattern of coordinated motion can be used, circular patterns are generally preferred because they are more easily produced.

U.S. Pat. No. 4,926,452 entitled "AUTOMATED LAMINOGRAPHY SYSTEM FOR INSPECTION OF ELECTRONICS", issued to Baker et al. describes a continuous circular scanned laminography system wherein the object remains stationary while the X-ray source and detector move in a coordinated circular pattern. The moving X-ray source comprises a microfocus X-ray tube wherein an electron beam is deflected in a circular scan pattern onto an anode target. The resulting motion of the X-ray source is synchronized with a rotating X-ray detector that converts the X-ray shadowgraph into an optical image so as to be viewed and integrated in a stationary video camera, thus forming a cross sectional image of the object. A computer system controls an automated positioning system that supports the item under inspection and moves successive areas of interest into view. In order to maintain high image quality, a computer system also controls the synchronization of the electron beam deflection and rotating optical system, making adjustments for inaccuracies of the mechanics of the system.

Laminographic cross sectional images may also be formed within the data memory of a computer by combining two or more individual images that were formed with coordinated positioning of two of the three main components comprising the laminography system, that is, a source, an object, and a detector. The images are combined within the computer memory such that any point in the object focal plane in one image is always combined with the same point in the object focal plane of another image, this other image consisting of a different angular view of the same object. If the individual views are taken with the detector describing a circular path, then the combined image formed from the individual images approaches the appearance of a continuous circular scanned image (as described in U.S. Pat. No. 4,926,452, discussed above) when the number of individual images is very large. Mathematically shifting the pixel combinations of the multiple individual images has the result of changing the location of the focal plane in the object. Thus, this method of generating a cross sectional image of an object has the advantage over moving and blurring methods, in that from one set of images, multiple laminographic cross sectional images of different focal planes may be formed. This technique has been called synthetic laminography, or computerized synthetic cross sectional imaging.

The laminography techniques described above are currently used in a wide range of applications including medical and industrial X-ray imaging. Laminography is particularly well suited for inspecting objects which comprise several layers having distinguishable features within each layer. However, some previous laminography systems which produce such cross sectional images typically experience shortcomings in resolution and/or speed of inspection, thus accounting for its rare implementation. These shortcomings are frequently due to the difficulties in achieving high speed coordinated motion of the source and detector to a degree of precision sufficient to produce a high resolution cross sectional image.

In a laminography system which views a fixed object and has a field of view which is smaller than the object being inspected, it may be necessary to move the object around within the field of view thus generating multiple laminographs which, when pieced together form an image of the entire object. This is frequently achieved by supporting the object on a mechanical handling system, such as an X, Y, Z positioning table. The table is then moved to bring the desired portions of the object into the field of view. Movement in the X and Y directions locates the area to be examined, while movement in the Z direction moves the object up and down to select the plane within the object where the cross sectional image is to be taken. While this method effectively enables various areas and planes of the object to be viewed, there are inherent limitations associated with the speed and accuracy of such mechanical motions. These constraints effectively act to increase the cycle time, thereby reducing the rates at which inspection can occur. Furthermore, these mechanical motions produce vibrations which tend to reduce the system resolution and accuracy.

U.S. Pat. No. 5,259,012 entitled "LAMINOGRAPHY SYSTEM AND METHOD WITH ELECTROMAGNETICALLY DIRECTED MULTIPATH RADIATION SOURCE", issued to Baker et al. describes a system which enables multiple locations within an object to be imaged without mechanical movement of the object. The object is interposed between a rotating X-ray source and a synchronized rotating detector. A focal plane within the object is imaged onto the detector so that a cross sectional image of the object is produced. The X-ray source is produced by deflecting an electron beam onto a target anode. The target anode emits X-ray radiation where the electrons are incident upon the target. The electron beam is produced by an electron gun which includes X and Y deflection coils for deflecting the electron beam in the X and Y directions. Deflection voltage signals are applied to the X and Y deflection coils and cause the X-ray source to rotate in a circular trace path. An additional DC voltage applied to the X or Y deflection coil will cause the circular path traced by the X-ray source to shift in the X or Y direction by a distance proportional to the magnitude of the DC voltage. This causes a different field of view, which is displaced in the X or Y direction from the previously imaged region, to be imaged.

Changes in the radius of the X-ray source path result in a change in the Z level of the imaged focal plane. This system solves many of the problems of the early laminography systems in the generation of high resolution and high speed cross sectional images. This system is an improvement over that described in U.S. Pat. No. 4,926,452 in that it allows for the inspection of objects that are larger than the field of view by electronically generating cross sectional images off-axis to the rotation of the source and detector, thus eliminating a major source of mechanical motion. Additionally, the selection of the focal plane is accomplished by electronically sizing the diameter of the circular scan, thus eliminating the mechanical Z motion from the system described in U.S. Pat. No. 4,926,452. The method of generating cross sectional images described in U.S. Pat. No. 5,259,012 can theoretically go twice as fast as the system described in U.S. Pat. No. 4,926,452, since it does not have to wait for mechanical motion. It does have the same limitations as the system described in U.S. Pat. No. 4,926,452 as to source power and spot size limitations. Thus, total inspection speed is only a two to three times improvement, while adding considerable complexity in electronic circuitry and calibration efforts. While the system described in U.S. Pat. No. 5,259,012 does not require an X, Y, or Z table to position the object under inspection, it still needs a very complex and large X-ray tube to enable the system to work. The diameter of the X-ray tube must be slightly larger than the largest horizontal dimension of the object to be inspected with cross sectional imaging. Otherwise, the object, or the detector and X-ray tube, must be moved in the X direction and/or the Y direction, to inspect the entire object. Another disadvantage of this system is the requirement that the rotary detector imaging system relies on spinning a mechanical assembly at 600 or more revolutions per minute (RPM).

U.S. Pat. No. 5,020,086 entitled "MICROFOCUS X-RAY SYSTEM", issued to Peugeot discloses a system for tomosynthesis wherein an object is scanned by an X-ray beam from a circular position on a target resulting from the electron beam being scanned in a circle by appropriate control signals from a beam controller and applied to the deflection coils of a microfocus X-ray tube. Tomosynthesis is accomplished by the well known method of in-register combination of a series of digital X-ray images produced by X-ray beams emanating from different locations. This is achieved by positioning an X-ray source at multiple points on a circle around a central axis. This system eliminates some of the mechanical motion required by the system described in U.S. Pat. No. 4,926,452, in that the detector does not have to rotate. However, practical limitations of pixel size and resolution tend to limit the Peugeot system to inspection of items with small fields of view. Additionally, the system still requires an X, Y table to position the object under the field of view. The speed of a commercial prototype of this system is not significantly faster than the system described in U.S. Pat. No. 5,259,012, but may have a slightly lower cost of manufacture.

While there has been some well received commercial success of the system described in U.S. Pat. No. 4,926,452, and some commercial interest in both the system described in U.S. Pat. No. 5,020,086 and the system described in U.S. Pat. No. 5,259,012, industry still desires a cross sectional inspection system which operates at an even higher inspection speed while costing less than the existing industrial cross sectional inspection systems. If a new cross sectional imaging system could meet the demands of low cost and high performance, the commercial applications and usage would grow rapidly over the current technology and the benefit to the electronics industry for circuit board inspection would be greatly increased.

Accordingly, several objects and advantages of the present invention are that it provides an improved, lower cost, and simpler way to achieve high speed and high resolution cross sectional imaging for the inspection of electrical connections, than do previous systems.

It is one object of the present invention to eliminate the costly and complex scanned beam type X-ray tube used in U.S. Pat. Nos. 5,020,086 and 5,259,012, and replace the scanned beam X-ray tube with a standard low cost X-ray system.

It is another object of the present invention to eliminate the expensive X, Y positioning table (U.S. Pat. No. 5,020,086) or the X, Y, Z table (U.S. Pat. No. 5,259,012) with a low cost, single axis, highly reliable, continuous motion system.

It is another object of the present invention to replace the large diameter, expensive, and highly complex X-ray tube and system used in the U.S. Pat. No. 5,259,012 system, with a standard low cost X-ray system.

It is another object of the present invention to replace the complex rotating detector systems described in U.S. Pat. Nos. 4,926,452 and 5,259,012, and the large diameter and expensive vacuum tube detector disclosed in U.S. Pat. No. 5,020,086, with conventional, highly reliable, solid state, mass produced, low cost, high performance, linear line scan type detectors.

SUMMARY OF THE INVENTION

The present invention comprises a greatly improved computerized laminography system which uses a continuous scan method for high speed, high resolution inspection. The system does not require motion of the detector, the X-ray tube, the spot of X-rays, or the beam of X-rays. The only motion required is a smooth linear motion of the object to be imaged. The present invention is faster than previous laminography systems for the inspection of electrical connections on a circuit board.

Circuit boards are fed into the X-ray laminography scanner at a rate of approximately 0.3 inches per second at a uniform velocity. The circuit boards are separated from each other by approximately 0.7 inches. The mechanism that provides the uniform linear motion is a moving chain belt that supports the circuit boards on their two opposite parallel sides.

The detector system includes a minimum of two (2) linear scanner detectors (preferably four (4) linear scanner detectors) symmetrically positioned at an angular relationship to the circuit board. The linear scanner detectors are mounted so that they are very close to the bottom of the board under test. Each linear scanner detector has a thin deposit of X-ray sensitive phosphor on the detector surface and achieves approximately 16 lp/mm resolution. Additionally, each linear scanner detector has built in electronics to provide an 8 to 16 bit data stream with digitizing electronics that interface directly to a personal computer (PC).

The X-ray source includes at least one source of X-rays (preferably two) collimated so that each X-ray tube gives off two fan beams of X-rays. The X-ray sources are mounted with respect to the circuit board to provide the preferred laminographic angle and at the preferred distance from the circuit board and linear scanner detectors such that the combination of their spot size and the board to detector standoff and X-ray power available all cooperate to provide a high resolution image on the detector having adequate light levels. The preferred source is a standard X-ray tube capable of operating at 125 kilovolts (KV) with an anode current in the range of approximately 0.1 milliamperes (ma) to 1.0 milliamperes. If two tubes are used, both tubes may be powered by a single high voltage (HV) power supply. The preferred focal spot size of the X-ray tube is in the range of approximately 100 microns to 1000 microns in diameter.

The data from each linear scanner detector is used to generate, within computer memory, a complete X-ray picture of the 8.5"×12" circuit board. In a 4 detector system, the minimum memory requirement is approximately 260 megabytes. For the system to analyze one circuit board while another image of a second circuit board is acquired requires an additional 260 megabytes of memory. Thus, a total of 520 megabytes of memory is required for a system having four linear scanner detectors and that acquires one set of four images while the previously acquired set of four images is being analyzed. It is preferred to have the computer memory designed in such a way that it can be switched over to the detectors for image gathering, then switched to a view analysis computer for generation of the slice image or images for analysis, however this is not essential.

Laminographic slices are generated by combining the four separate images by shifting the pixel locations in X and Y to correspond to a specific focal plane in the object. Any number of focal planes may be generated from a single set of four images by this process.

The laminographic images are then analyzed in a conventional way to yield data about the quality of the electrical connection on the circuit board.

In a first embodiment, the invention is an imaging system comprising: a first X-ray source; a first linear X-ray detector positioned to intercept X-rays emitted by the first X-ray source at a first angle; a second linear X-ray detector positioned to intercept X-rays emitted by the first X-ray source at a second angle; a linear motion system positioned between the first X-ray source and the first and second linear X-ray detectors, the linear motion system further having a support for an object under test, the linear motion system configured to transport the object under test through the X-rays emitted at the first angle and the second angle and detected by the first linear X-ray detector and the second linear X-ray detector, respectively, after having passed through the object under test, thereby forming a first shadowgraph image and a second shadowgraph image of the object under test; and a control system connected to the linear motion system, the first linear X-ray detector and the second linear X-ray detector, wherein the control system regulates the linear motion system and the formation of the first and second shadowgraph images to produce a laminographic cross sectional image of a cutting plane of the object under test. This embodiment may further comprise a first collimator positioned with respect to the first X-ray source such that the first collimator is configured to direct X-rays emitted by the first X-ray source toward the first linear X-ray detector and to block X-rays travelling in other directions. Additionally, this imaging system may further comprise a second collimator positioned with respect to the first X-ray source such that the second collimator is configured to direct X-rays emitted by the first X-ray source toward the second linear X-ray detector and to block X-rays travelling in other directions. In some configurations, the imaging system further comprises a second X-ray source laterally positioned with respect to the first X-ray source; a third linear X-ray detector positioned to intercept X-rays emitted by the second X-ray source at a third angle; and a fourth linear X-ray detector positioned to intercept X-rays emitted by the second X-ray source at a fourth angle. In certain configurations, the imaging system further comprises a third collimator positioned with respect to the second X-ray source such that the third collimator is configured to direct X-rays emitted by the second X-ray source toward the third linear X-ray detector and to block X-rays travelling in other directions. Similarly, a fourth collimator may be positioned with respect to the second X-ray source such that the fourth collimator is configured to direct X-rays emitted by the second X-ray source toward the fourth linear X-ray detector and to block X-rays travelling in other directions. The first, second, third and fourth linear X-ray detectors may further comprise monolithic, self-scanning, linear, photodiode arrays. Additionally, an X-ray scintillation material may be deposited on the first, second, third and fourth linear photodiode array X-ray detectors. The X-ray scintillation material further comprise gadolinium oxysulfide. The linear motion system in some configurations comprises a conveyor belt.

In a second embodiment, the invention is an apparatus for producing cross sectional images of a cutting plane within an object comprising: a linear motion system adapted to support and transport an object under test along a substantially linear path; a first source of X-rays for producing X-rays, the first source of X-rays positioned adjacent to the linear motion system such that the X-rays produced by the first X-ray source impinge upon a first surface of the object and scan the object as the linear transport system moves the object along the linear path; a first linear X-ray detector comprising a plurality of X-ray detector elements positioned adjacently in a substantially linear fashion, the first linear X-ray detector positioned adjacent a second surface of the object substantially opposite the first surface, the first linear X-ray detector thereby intercepting and detecting X-rays which enter the object through the first surface and exit the object through the second surface, the first linear X-ray detector positioned at a first angle with respect to the first source of X-rays; a first linear X-ray detector readout control system, the first linear X-ray detector readout control system further having a clock which controls the periodic reading and storing of signals produced by the plurality of X-ray detector elements; a second linear X-ray detector positioned a distance away from the first linear X-ray detector, the second linear X-ray detector comprising a plurality of X-ray detector elements positioned adjacently in a substantially linear fashion, the second linear X-ray detector positioned adjacent the second surface of the object substantially opposite the first surface, the second linear X-ray detector thereby intercepting and detecting X-rays which enter the object through the first surface and exit the object through the second surface, the second linear X-ray detector positioned at a second angle with respect to the first source of X-rays; a second linear X-ray detector readout control system, the second linear X-ray detector readout control system further having a clock which controls the periodic reading and storing of signals produced by the plurality of X-ray detector elements; a control system which controls and coordinates the operation of the linear motion system and the first and second linear X-ray detector readout control systems such that the first linear X-ray detector produces a first X-ray shadowgraph image of the object and the second linear X-ray detector produces a second X-ray shadowgraph image of the object; and an image analysis system which receives the first and second X-ray shadowgraph images of the object and combines the first and second X-ray shadowgraph images of the object to form a cross sectional image of a cutting plane of the object. In some configurations, the apparatus further comprises a first collimator positioned with respect to the first source of X-rays such that the first collimator is configured to direct X-rays emitted by the first source of X-rays toward the first linear X-ray detector and to block X-rays travelling in other directions. Similarly, a second collimator may be positioned with respect to the first source of X-rays such that the second collimator is configured to direct X-rays emitted by the first source of X-rays toward the second linear X-ray detector and to block X-rays travelling in other directions. In some configurations, this apparatus further comprising a second source of X-rays laterally positioned with respect to the first source of X-rays; a third linear X-ray detector positioned to intercept X-rays emitted by the second source of X-rays at a third angle; and a fourth linear X-ray detector positioned to intercept X-rays emitted by the second source of X-rays at a fourth angle. Similarly, a third collimator may positioned with respect to the second source of X-rays such that the third collimator is configured to direct X-rays emitted by the second source of X-rays toward the third linear X-ray detector and to block X-rays travelling in other directions a fourth collimator may be positioned with respect to the second source of X-rays such that the fourth collimator is configured to direct X-rays emitted by the second source of X-rays toward the fourth linear X-ray detector and to block X-rays travelling in other directions. In some configurations, the first, second, third and fourth linear X-ray detectors further comprise monolithic, self-scanning, linear, photodiode arrays. An X-ray scintillation material may be deposited on the first, second, third and fourth linear photodiode array X-ray detectors. In some embodiments, the X-ray scintillation material further comprises gadolinium oxysulfide. The linear motion system may comprise a conveyor belt.

In a third embodiment, the invention is a method of producing a cross sectional image of an object comprising the steps of: providing a first source of X-rays; detecting X-rays produced by the first source of X-rays with a first linear X-ray detector after the X-rays have impinged upon and penetrated the object from a first angular orientation; detecting X-rays produced by the first source of X-rays with a second linear X-ray detector after the X-rays have impinged upon and penetrated the object from a second angular orientation; moving the object between the first source of X-rays and the first and second linear X-ray detectors along a substantially linear path; producing a first X-ray shadowgraph image of the object with the X-rays detected by the first linear X-ray detector as the object traverses the substantially linear path between the first source of X-rays and the first linear X-ray detector; producing a second X-ray shadowgraph image of the object with the X-rays detected by the second linear X-ray detector as the object traverses the substantially linear path between the first source of X-rays and the second linear X-ray detector; and combining the first and second X-ray shadowgraph images of the object to form a cross sectional image of the object. In some configurations, the method further comprises the step of collimating the first source of X-rays with a first collimator configured to direct X-rays emitted by the first source of X-rays toward the first linear X-ray detector and to block X-rays travelling in other directions. Similarly, the method may further comprise the step of collimating the first source of X-rays with a second collimator configured to direct X-rays emitted by the first source of X-rays toward the second linear X-ray detector and to block X-rays travelling in other directions. In some configurations, the method further comprises the steps of: providing a second source of X-rays; and positioning the second source of X-rays laterally with respect to the first source of X-rays; detecting X-rays produced by the second source of X-rays with a third linear X-ray detector after the X-rays have impinged upon and penetrated the object from a third angular orientation; and detecting X-rays produced by the second source of X-rays with a fourth linear X-ray detector after the X-rays have impinged upon and penetrated the object from a fourth angular orientation. This method may further include the steps of: collimating the second source of X-rays with a third collimator configured to direct X-rays emitted by the second source of X-rays toward the third linear X-ray detector and to block X-rays travelling in other directions; and collimating the second source of X-rays with a fourth collimator configured to direct X-rays emitted by the second source of X-rays toward the fourth linear X-ray detector and to block X-rays travelling in other directions.

In a fourth embodiment, the invention is an imaging system comprising: a first X-ray source; a first linear X-ray detector positioned to intercept X-rays emitted by the first X-ray source at a first angle; a second linear X-ray detector positioned to intercept X-rays emitted by the first X-ray source at a second angle; a linear motion system to which the first X-ray source and the first and second linear X-ray detectors are mounted, the linear motion system further having a path for a stationary object under test to pass, the linear motion system configured to transport the first X-ray source and the first and second linear X-ray detectors past the stationary object under test such that the X-rays emitted at the first angle and the second angle and detected by the first linear X-ray detector and the second linear X-ray detector, respectively, after having passed through the stationary object under test, thereby form a first shadowgraph image and a second shadowgraph image of the stationary object under test; and a control system connected to the linear motion system, the first linear X-ray detector and the second linear X-ray detector, wherein the control system regulates the linear motion system and the formation of the first and second shadowgraph images to produce a laminographic cross sectional image of a cutting plane of the stationary object under test. In some configurations, a first collimator is positioned with respect to the first X-ray source such that the first collimator is configured to direct X-rays emitted by the first X-ray source toward the first linear X-ray detector and to block X-rays travelling in other directions. Similarly, a second collimator may be positioned with respect to the first X-ray source such that the second collimator is configured to direct X-rays emitted by the first X-ray source toward the second linear X-ray detector and to block X-rays travelling in other directions. In certain configurations, the imaging system further comprises: a second X-ray source positioned on the linear motion system laterally with respect to the first X-ray source; a third linear X-ray detector positioned on the linear motion system to intercept X-rays emitted by the second X-ray source at a third angle; and a fourth linear X-ray detector positioned on the linear motion system to intercept X-rays emitted by the second X-ray source at a fourth angle.

In a fifth embodiment, the invention includes a method of producing a cross sectional image of a stationary object comprising the steps of: providing a first source of X-rays; detecting X-rays produced by the first source of X-rays with a first linear X-ray detector after the X-rays have impinged upon and penetrated the stationary object from a first angular orientation; detecting X-rays produced by the first source of X-rays with a second linear X-ray detector after the X-rays have impinged upon and penetrated the stationary object from a second angular orientation; moving the first source of X-rays and the first and second linear X-ray detectors along a substantially linear path past the stationary object such that the X-rays from the first source of X-rays penetrate the stationary object and are detected by the first and second linear X-ray detectors; producing a first X-ray shadowgraph image of the stationary object with the X-rays detected by the first linear X-ray detector as the first linear X-ray detector and the first source of X-rays traverse the substantially linear path past the stationary object; producing a second X-ray shadowgraph image of the stationary object with the X-rays detected by the second linear X-ray detector as the second linear X-ray detector and the first source of X-rays traverse the substantially linear path past the stationary object; and combining the first and second X-ray shadowgraph images of the stationary object to form a cross sectional image of the stationary object. In some configurations, the method further comprises the steps of: collimating the first source of X-rays with a first collimator configured to direct X-rays emitted by the first source of X-rays toward the first linear X-ray detector and to block X-rays travelling in other directions; and collimating the first source of X-rays with a second collimator configured to direct X-rays emitted by the first source of X-rays toward the second linear X-ray detector and to block X-rays travelling in other directions. In some configurations, the method further comprises the steps of: providing a second source of X-rays; and positioning the second source of X-rays laterally with respect to the first source of X-rays. This method may further include the steps of: detecting X-rays produced by the second source of X-rays with a third linear X-ray detector after the X-rays have impinged upon and penetrated the stationary object from a third angular orientation; and detecting X-rays produced by the second source of X-rays with a fourth linear X-ray detector after the X-rays have impinged upon and penetrated the stationary object from a fourth angular orientation.

These and other characteristics of the present invention will become apparent through reference to the following detailed description of the preferred embodiments and accompanying drawings.

DETAILED DESCRIPTION OF THE PREFERRED EMBODIMENTS

Figure 1:
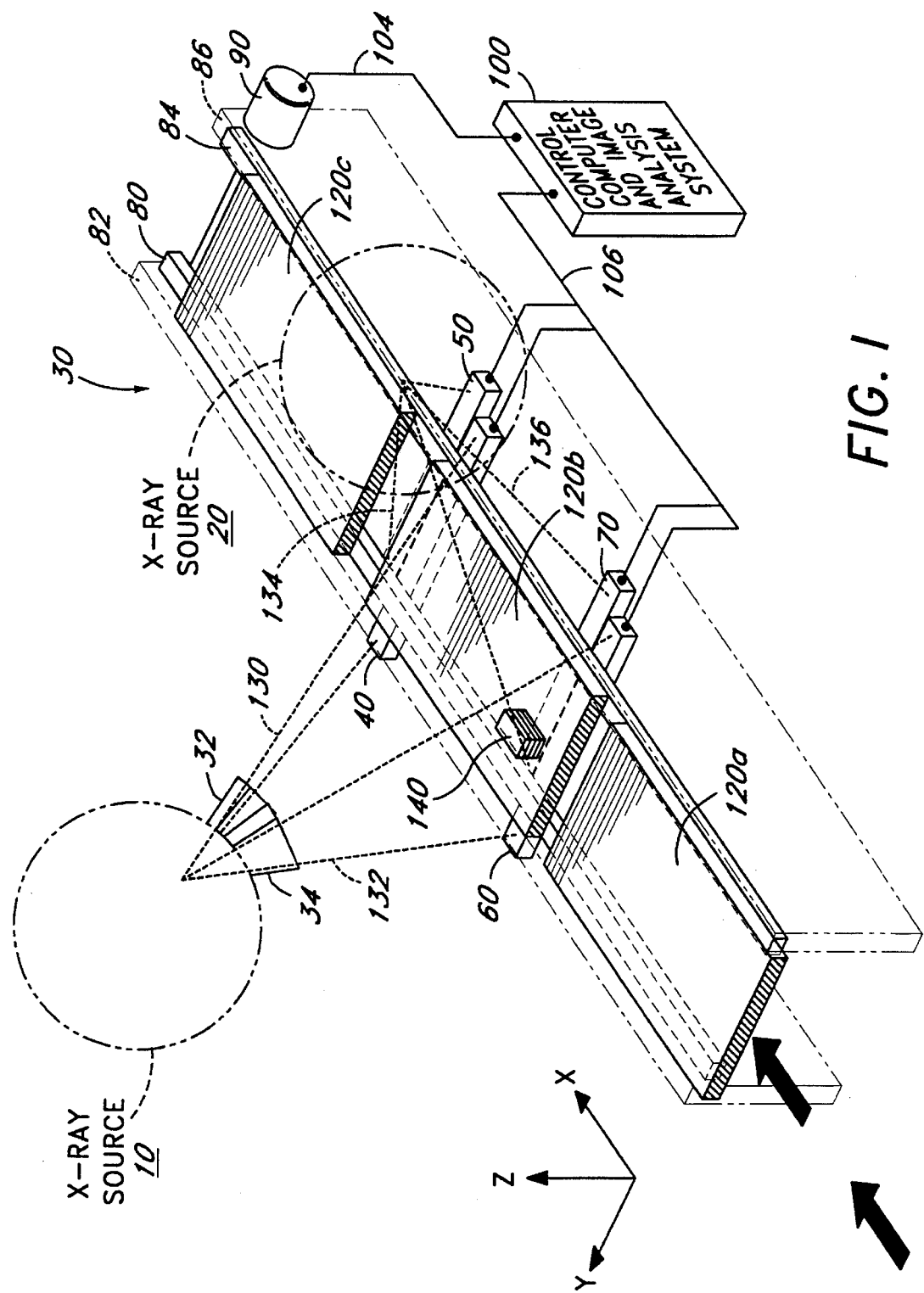
FIG. 1 shows a perspective view of a continuous linear scan laminography system in accordance with the present invention.

Shown in FIGS. 1, 2, 3 and 4 are a perspective view, a top view, a side view and an end view, respectively, of a continuous linear scan laminography system in accordance with the present invention. Referring to FIGS. 1, 2, 3 and 4, a first X-ray source 10 and a second X-ray source 20 are positioned above and along opposing sides of a conveyor system 30. The first X-ray source 10 includes a front collimator 32 and a rear collimator 34. Similarly, the second X-ray source 20 includes a front collimator 36 and a rear collimator 38. A first linear X-ray detector 40 is located adjacent to a second linear X-ray detector 50 to the right (positive X-direction) of a centerline (not shown) along the Y-direction defined by connecting the first X-ray source 10 with the second X-ray source 20. A third linear X-ray detector 60 is located adjacent to a fourth linear X-ray detector 70 to the left (negative X-direction) of the centerline connecting the first and second X-ray sources 10, 20. Each of the first, second, third and fourth linear X-ray detectors 40, 50, 60, 70 are located below the conveyor system 30. Conveyor system 30 further includes a first chain drive mechanism 80 and a first guide rail 82 on a first side and a second chain drive mechanism 84 and a second guide rail 86 on a second side. A synchronized drive motor 90 is connected to the first and second chain drive mechanisms 80, 84. The synchronized drive motor 90 is connected to a control computer and image analysis system 100 by motor power and control lines 104. The control computer and image analysis system 100 is also connected to the first, second, third and fourth linear X-ray detectors 40, 50, 60, 70 by means of detector power, control and signal lines 106.

Figure 2:
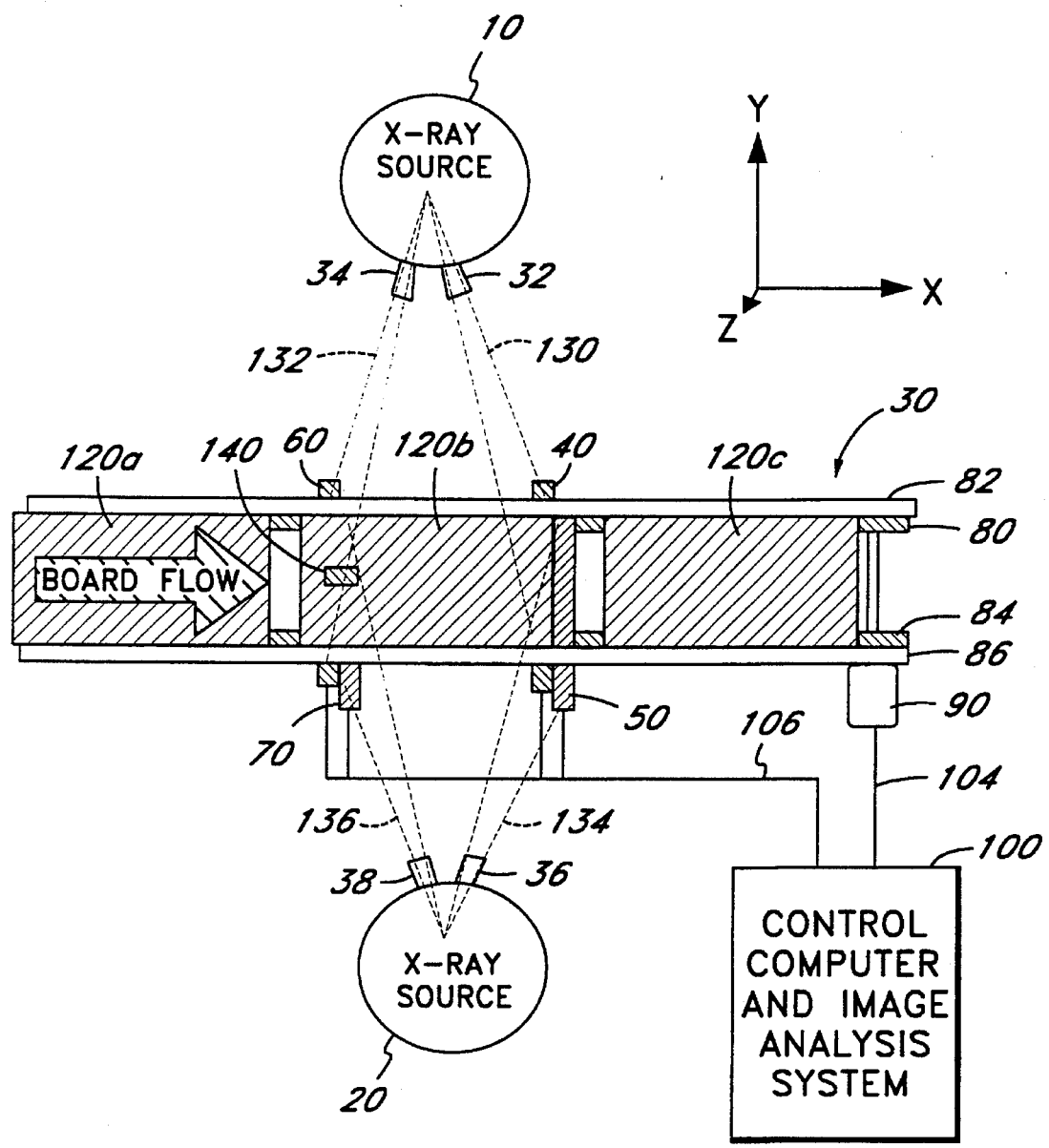
FIG. 2 shows a top view of the continuous linear scan laminography system of FIG. 1.
Figure 3:
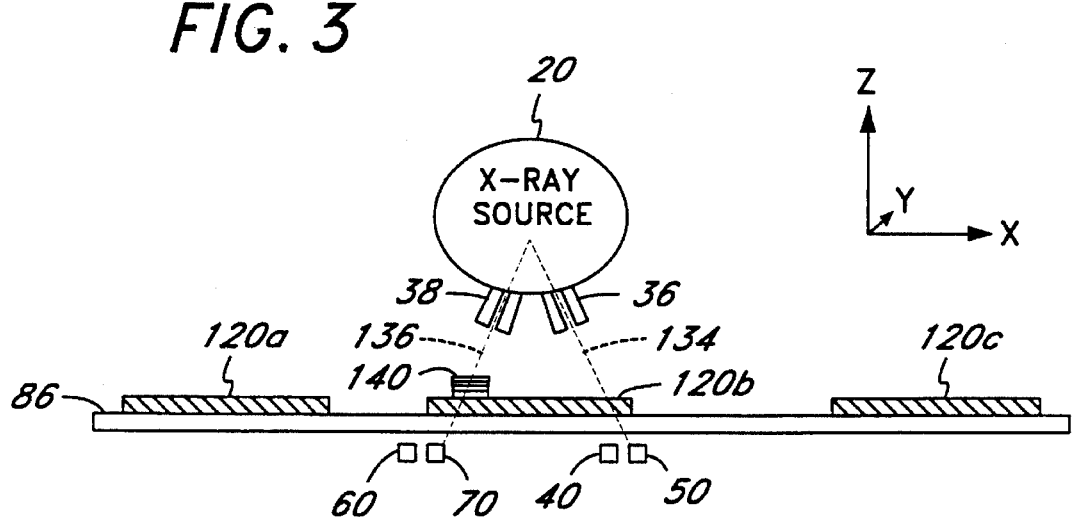
FIG. 3 shows a side view of the continuous linear scan laminography system shown in FIGS. 1 and 2.

In operation, circuit boards 120a, 120b, 120c are positioned onto the chain drive mechanisms 80, 84 and guided through the conveyor system 30 by the guide rails 82, 86. For purposes of describing the operation of the invention, the size of the circuit boards 120 is taken to be approximately 8.5 inches by 12 inches. Other sizes may also be used and these dimensions are in no way meant to be limiting. The circuit boards 120a, 120b, 120c are smoothly advanced by the chain drive mechanisms 80, 84 at a constant velocity of approximately 0.3 inches per second by the synchronized drive motor 90. The circuit boards 120a, 120b, 120c are separated from each other by approximately 0.7 inches. The synchronized drive motor 90 is operated by the control and image analysis computer 100 through the motor power and control lines 104. As shown in FIGS. 1 and 2: a) the inspection of circuit board 120c has been completed; b) the inspection of circuit board 120b is in progress; and c) circuit board 120a has just been loaded onto the conveyor system 30 and will be inspected immediately after the inspection of circuit board 120b is complete.

X-RAY GENERATION AND COLLIMATION

The X-ray sources 10 and 20 are collimated by collimators 32, 34, 36, 38 to limit the angular spread of radiation emitted by the first and second X-ray sources 10, 20 in both the X-direction and the Y-direction so that each X-ray source 10, 20 produces two fan beams of X-rays. The first X-ray source 10 gives off fan beams of X-rays 130, 132 while the second X-ray source 20 gives off fan beams of X-rays 134, 136. The X-ray sources 10, 20 are mounted in a conventional manner at a location which provides appropriate laminographic angles for production of cross sectional images of the circuit board 120b. For example, as can be seen in FIGS.

1 and 4, the X-ray sources 10, 20 are located at angles of approximately ±45 degrees with respect to the normal to the circuit board 120b (Z-direction). Additionally, the X-ray sources 10, 20 are located a distance from the circuit board 120b and linear X-ray detectors 40, 50, 60, 70 such that the combination of: 1) the focal spot sizes of the X-ray sources 10, 20; 2) the standoff distance between the circuit board 120b and the linear X-ray detectors 40, 50, 60, 70 (typically one inch or less); and 3) the power output of the X-ray sources 10, 20; all cooperate to provide sufficient light levels at the linear X-ray detectors 40, 50, 60, 70 to produce high resolution images.

The preferred X-ray sources 10, 20 are standard industrial X-ray tubes operable at voltages up to 125 kilovolts with an anode current ranging from approximately 0.1 ma to 1.0 ma. The first and second X-ray tubes 10, 20 may both be powered by a single high voltage (HV) power supply (not shown). The preferred focal spot size of the X-ray tubes 10, 20 is in the range of from 100 microns to 1000 microns in diameter.

Figure 4:
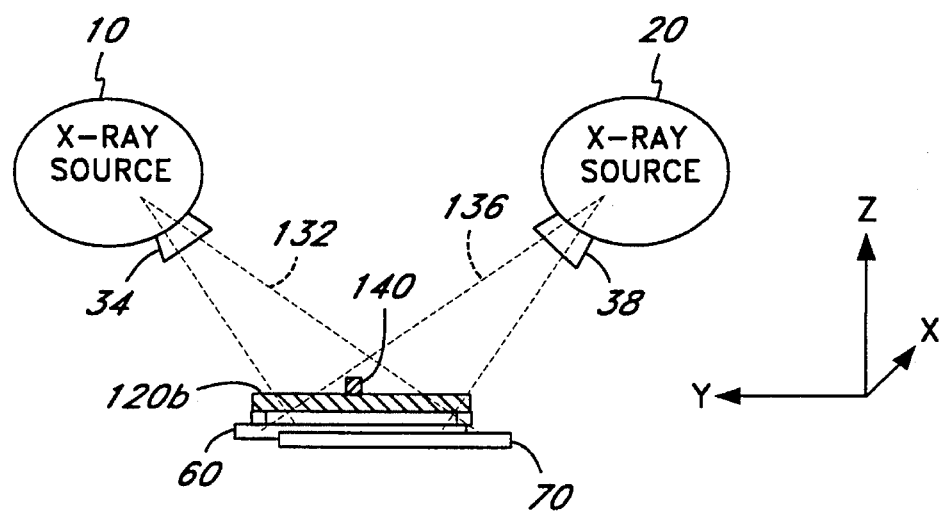
FIG. 4 shows an end view from the circuit board loading end of the continuous linear scan laminography system shown in FIGS. 1, 2 and 3.

The circuit board 120b being inspected is irradiated by X-rays generated by X-ray sources 10, 20. The angular spread of the X-rays emitted from the first X-ray source 10 are: 1) collimated in the X-direction by the front collimator 32 into the narrow fan beam of X-rays 130 configured to illuminate only a first small portion of the circuit board 120b and the front surface of the first linear X-ray detector 40 after having passed through the first small portion of the circuit board 120b illuminated; and 2) collimated in the X-direction by the rear collimator 34 into the narrow fan beam of X-rays 132 configured to illuminate only a third small portion of circuit board 120b and the front surface of the third linear X-ray detector 60 after having passed through the third small portion of circuit board 120b. Similarly, X-rays emitted from the second X-ray source 20 are: 1) collimated in the X-direction by the front collimator 36 into the narrow fan beam of X-rays 134 configured to illuminate only a second small portion of the circuit board 120b and the front surface of the second linear X-ray detector 50 after having passed through the second small portion of circuit board 120b; and 2) collimated in the X-direction by the rear collimator 38 into the narrow fan beam of X-rays 136 configured to illuminate only a fourth small portion of the circuit board 120b and the front surface of the fourth linear X-ray detector 70 after having passed through the fourth small portion of the circuit board 120b. Thus, the first linear X-ray detector 40 receives only X-rays generated by the first X-ray source 10 and emitted through the front collimator 32; the second linear X-ray detector 50 receives only X-rays generated by the second X-ray source 20 and emitted through the front collimator 36; the third linear X-ray detector 60 receives only X-rays generated by the first X-ray source 10 and emitted through the rear collimator 34; and the fourth linear X-ray detector 70 receives only X-rays generated by the second X-ray source 20 and emitted through the rear collimator 38. Additionally, as best illustrated in FIGS. 2 and 4, each of the narrow fan beams of X-rays 130, 132, 134, 136 is collimated in the Y-direction by its respective collimator 32, 34, 36, 38 in a manner which prevents X-rays from extending beyond the horizontal extent (Y-direction) of its respective linear X-ray detector 40, 50, 60, 70.

X-RAY DETECTION, IMAGE FORMATION AND DATA HANDLING

The conveyor system 30 transports the circuit board under test 120b through the four collimated fan beams of X-rays 130, 132, 134, 136. X-rays which pass through the circuit board 120b are detected by the linear X-ray detectors 40, 50, 60, 70. Each linear X-ray detector 40, 50, 60, 70 converts the pattern of X-rays that have passed through the circuit board under test 120b into an electrical signal that is sent over the detector power, control, and signal lines 106 to the control computer and image analysis system 100 for processing.

The linear X-ray detectors 40, 50, 60, 70 in the preferred embodiment are approximately 8.5 inches wide and have a horizontal resolution (X-direction) of approximately 16–20 line pair/millimeter (lp/mm) resolution. This corresponds to 400 to 500 line pair/inch or 800 to 1000 dots per inch in the terminology of desk top scanning. Each of the linear X-ray detectors 40, 50, 60, 70 has built in digitizing electronics for providing a digitized data stream of 8 to 16 bits which interfaces directly to the control computer and image analysis system 100. The linear X-ray detectors 40, 50, 60, 70 are formed from standard line scan detectors used in desk top publishing scanners. Each linear X-ray detector 40, 50, 60, 70 has a thin coating of X-ray sensitive phosphor deposited directly on the front of the detector's light sensitive area. Typically, the X-ray sensitive phosphor is gadolinium oxysulfide, however, other materials may also be used, for example, cadmium tungstate. The data from each linear X-ray detector 40, 50, 60, 70 generates a complete X-ray shadowgraph picture of the 8.5" by 12" circuit board under test 120b as it passes over the respective detector. (See FIGS. 6a–6d)

The linear X-ray detectors 40, 50, 60, 70 are similar to charge coupled devices (CCD) commonly found in video cameras. The charge coupled devices used in video cameras are typically solid state integrated circuit chips having a two dimensional array of discrete light sensitive elements formed thereon. The linear X-ray detectors 40, 50, 60, 70 are linear or one dimensional arrays of discrete light sensitive elements formed on a single chip. Linear arrays are commonly used in baggage scanners at airport security stations to produce low resolution X-ray shadowgraph images of baggage.

One suitable linear X-ray detector, known as the Radiographic Line Scan (RLS) detector, is available commercially from Bio-Imaging Research, Inc. in Lincolnshire, Ill. A paper by Charles R. Smith and Joseph W. Erker, entitled; "Low cost, high resolution x-ray detector system for digital radiography and computed tomography"; *SPIE X-Ray Detector Physics and Applications II*, Vol. 2009, 1993, pp. 31–35, includes a detailed description of this device. Another suitable linear detector, known as the IL-C8-6000 Turbosensor, is available from Dalsa in Waterloo, Canada. Another producer of linear arrays is E G & G Reticon which produces a diode array, model number RL2048S, which is a monolithic self-scanning linear photodiode array with 2048 photodiode sensor elements with 25 micron center-to-center spacing. This device consists of a row of photodiodes, each with an associated storage capacitor on which to integrate photo current and a multiplex switch for readout by an independent integrated shift register. Thus, there several sources of commercially available linear array devices which can be adapted for use in the present invention.

While it is preferred that each of the 8.5" long linear X-ray detectors 40, 50, 60, 70 be a single unit, one skilled in the art will recognize that shorter units may be combined to achieve any desired overall length. That is, two of the above mentioned IL-C8-6000 Turbosensors, each of which is 6" long, may be mounted slightly staggered so that the end of one matches up to the end of the other, thus providing coverage for a 12 inch wide circuit board. Alternatively, a lens system or fiber optic reducer may be positioned between an X-ray scintillation screen of the desired length and the linear sensor of a shorter length. The image produced on the screen is then focused by the lens system onto the linear sensor having a shorter length or directed by appropriate reducing fiber optics onto the linear sensor.

The data from the linear X-ray detectors 40, 50, 60, 70 is stored in a memory bank within the control computer and image analysis system 100. For a system having a resolution of 800 DPI and an 8.5 inch width, there are 6800 pixels along the 8.5 inch width (X-direction), corresponding to the width of the circuit board under test 120b. At 800 DPI resolution, the 12 inch length of the circuit board under test 120b corresponds to 9600 pixels along the length direction (Y-direction). Thus, the memory bank used to store the complete image of the 8.5" by 12" circuit board 120b needs to have a storage capacity of 6800×9600×8 bits or approximately 65 megabytes. Since there are 4 linear X-ray detectors 40, 50, 60, 70, a total of 260 megabytes of memory is required. Additionally, if the system is to analyze the images for one circuit board 120c while the system acquires the images of the next circuit board 120b, the memory bank within the control computer and image analysis system 100 must be doubled for a total of 520 megabytes. The memory bank is designed in such a way that a first half of the memory bank is connected to the linear X-ray detectors 40, 50, 60, 70 while an image is being acquired while a second half of the memory bank, which contains the images for the previous circuit board, is connected to the image analysis portion of the control computer and image analysis system 100. When the image acquisition into the first half of the memory bank and the image analysis of the data in the second half of the memory bank are complete, the first half of the memory bank is disconnected from the linear X-ray detectors 40, 50, 60, 70 and connected to the image analysis portion of the control computer and image analysis system 100. Likewise, the second half of the memory bank is disconnected from the image analysis portion of the control computer and image analysis system 100 and connected to the linear X-ray detectors 40, 50, 60, 70.

LAMINOGRAPHIC CROSS SECTIONAL IMAGE FORMATION

As previously described, each of the first, second, third and fourth linear X-ray detectors 40, 50, 60, 70 produces a conventional X-ray shadowgraph image of the object being inspected, for example, a circuit board 120b. A laminographic cross sectional image of the object is formed from the four resulting shadowgraph images in a conventional manner. This technique is discussed in detail in U.S. Pat. No. 3,818,220 entitled "VARIABLE DEPTH LAMINAGRAPHY", issued to Richards and U.S. Pat. No. 3,499,146 entitled "VARIABLE DEPTH LAMINAGRAPHY WITH MEANS FOR HIGHLIGHTING THE DETAIL OF SELECTED LAMINA", issued to Richards.

Figure 5:
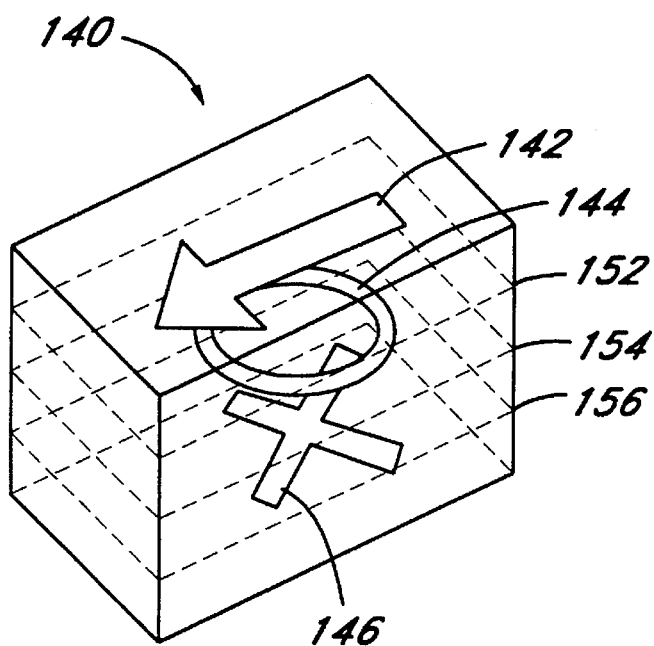
FIG. 5 shows a test object for demonstrating laminography.

FIG. 5 shows a test object 140 for illustrating the technique of creating a laminographic cross sectional image of a selected plane within the test object 140 from four shadowgraph images 160, 260, 360, 460 (see FIGS. 6a–6d). The test object 140 contains patterns in the shape of an arrow 142, a circle 144 and a cross 146 embedded within the test object 140 in three different planes 152, 154 and 156, respectively.

Figure 6A:
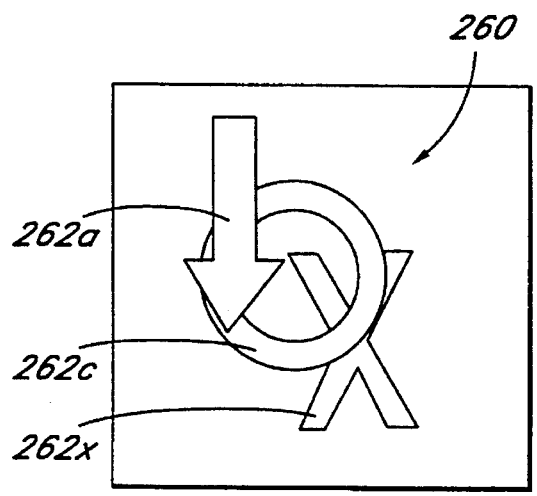
FIGS. 6a–6d show conventional shadowgraph images of the test object shown in FIG. 5 formed in each of four linear X-ray detectors.
Figure 6B:
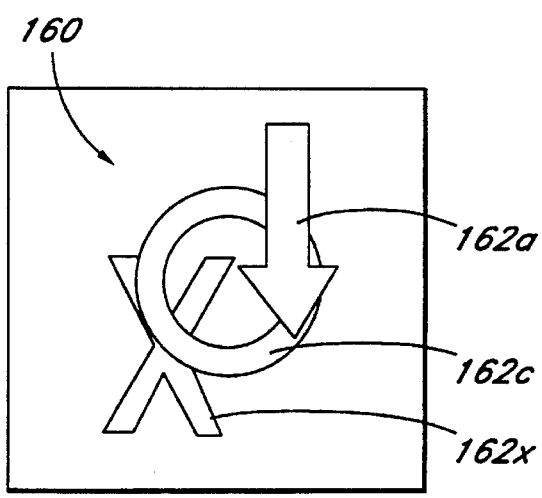
Figure 6C:
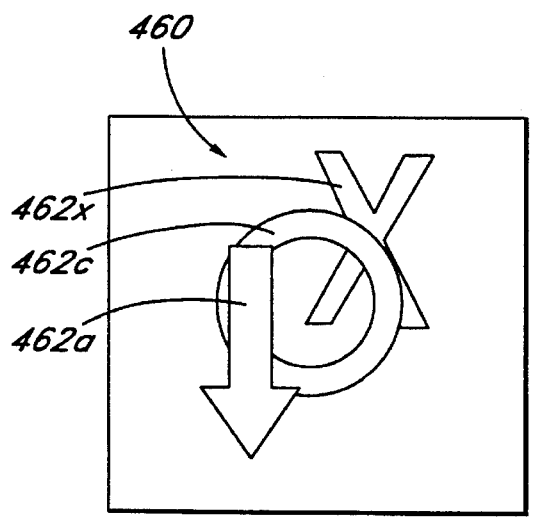
Figure 6D:
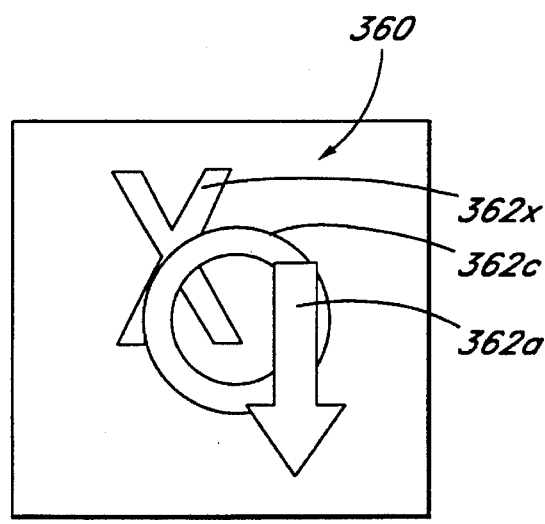

Shown in FIGS. 6a–6d are the shadowgraph images created by the four linear X-ray detectors 40, 50, 60, 70. The test object 140 is oriented on the conveyor system 30 as shown in FIGS. 1–4 with the arrow 142 pointing in the negative X-direction, i.e., toward the circuit board 120a. FIG. 6b shows a shadowgraph image 160 of the test object 140 created by the first linear X-ray detector 40. The arrow 142 forms an image 162a, the circle 144 forms an image 162c and the cross 146 forms an image 162x. FIG. 6a shows a shadowgraph image 260 of the test object 140 created by the second linear X-ray detector 50. The arrow 142 forms an image 262a, the circle 144 forms an image 262c and the cross 146 forms an image 262x. FIG. 6d shows a shadowgraph image 360 of the test object 140 created by the third linear X-ray detector 60. The arrow 142 forms an image 362a, the circle 144 forms an image 362c and the cross 146 forms an image 362x. FIG. 6c shows a shadowgraph image 460 of the test object 140 created by the fourth linear X-ray detector 70. The arrow 142 forms an image 462a, the circle 144 forms an image 462c and the cross 146 forms an image 462x.

Figure 7:
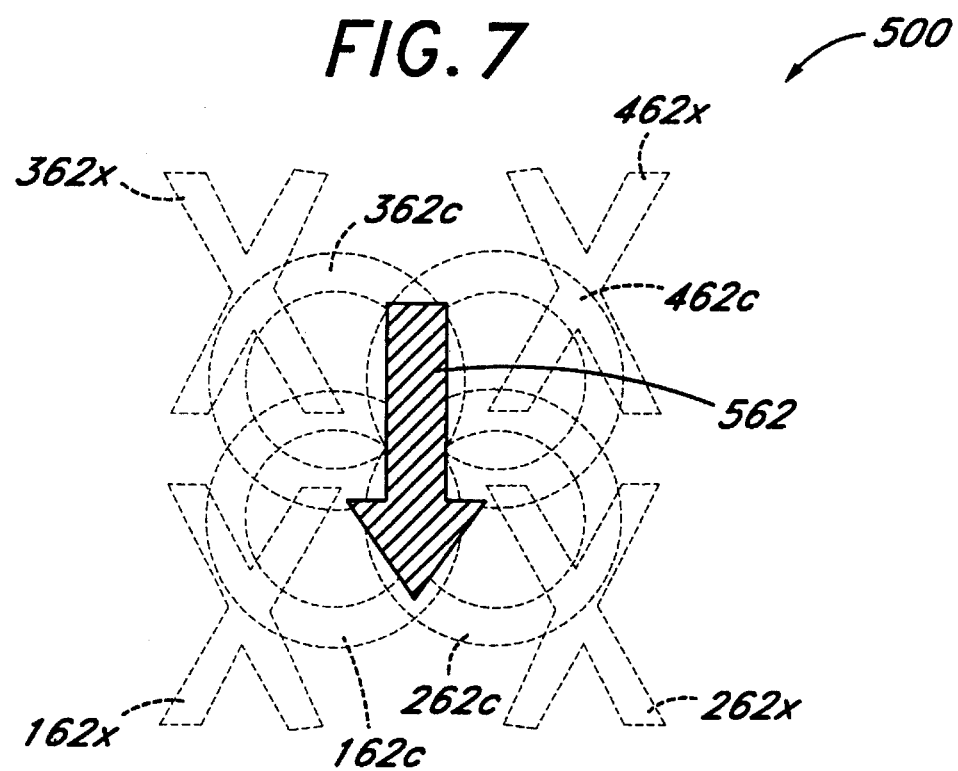
FIG. 7 shows a cross sectional laminographic image of the test object at one focal plane derived from the combination of the conventional shadowgraph images shown in FIGS. 6a–6d.

The formation of a laminographic cross sectional image of a selected plane within the test object 140 from the four shadowgraph images 160, 260, 360, 460 is accomplished by adding the four shadowgraph images 160, 260, 360, 460 together in a way which reinforces the images in selected plane at the sacrifice of the images in the other planes. The manner in which the four shadowgraph images 160, 260, 360, 460 are added together to form a laminographic cross sectional image 500 of the arrow 142 in the plane 152 is shown in FIG. 7. As illustrated in FIG. 7, each of the four shadowgraph images 160, 260, 360, 460 is shifted by a distance appropriate for each respective image in the X-direction and/or the Y-direction by a distance which causes the four images of the arrow 162a, 262a, 362a, 462a to substantially overlap one another thereby forming a reinforced image of the arrow 562 in the laminographic cross sectional image 500. The area surrounding the reinforced image of the arrow 562 is comprised of the four images of the circle 162c, 262c, 362c, 462c and the four images of the cross 162x, 262x, 362x, 462x. Since the images of the circle and the cross are scattered about at different locations, they do not reinforce each other as do the overlapping images of the arrow 162a, 262a, 362a, 462a. In a similar manner, the four shadowgraph images 160, 260, 360, 460 may be added together to form laminographic cross sectional images of the circle 144 in the plane 154 or the cross 146 in the plane 156 or any other preselected plane within the test object 140.

Figure 8:
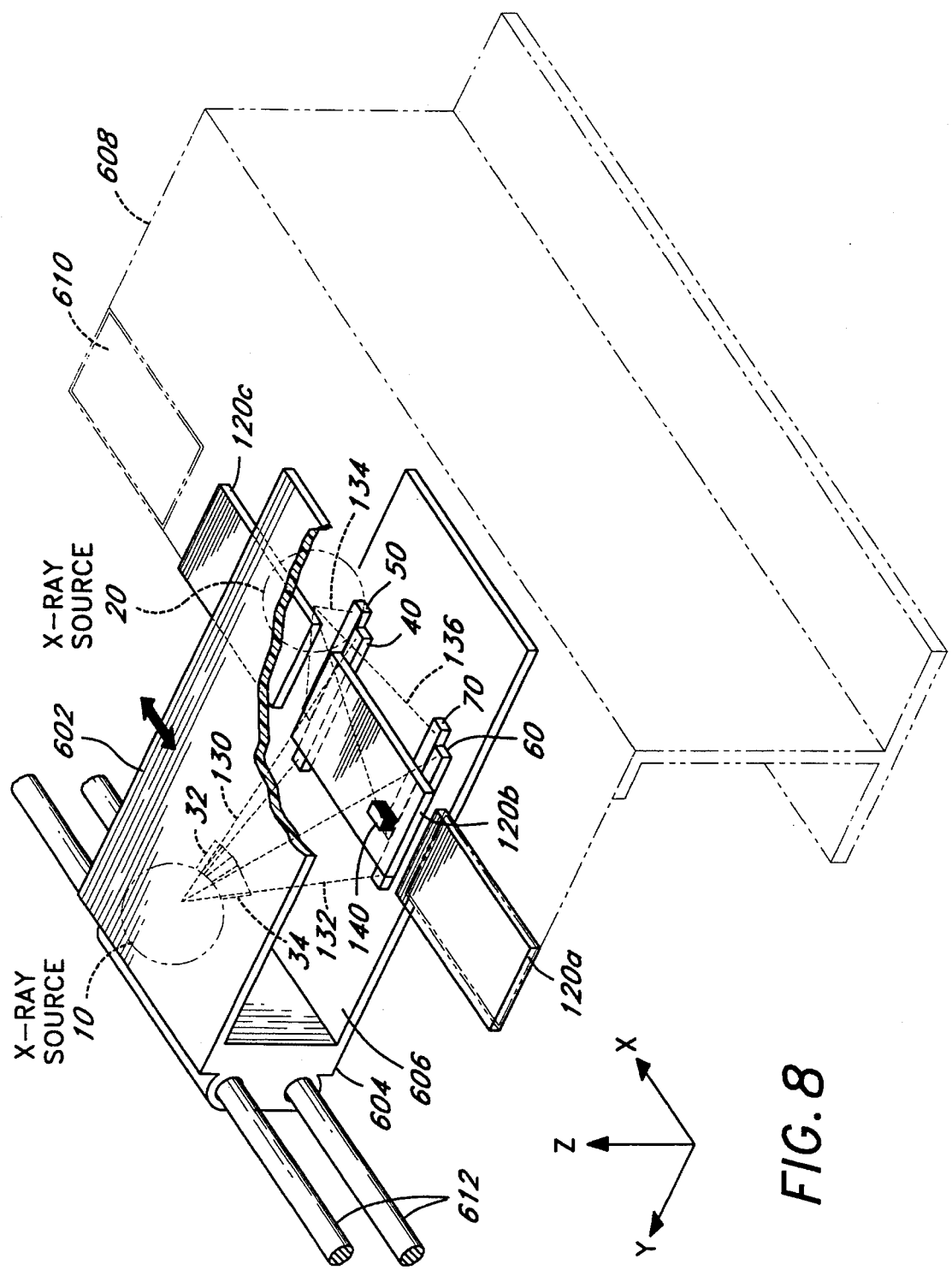
FIG. 8 shows a perspective view of an alternate embodiment of a continuous linear scan laminography system in accordance with the present invention.

The above described preferred embodiment describes a continuous scan apparatus and method for high speed, high resolution inspection which does not require motion of the detector, the X-ray tube, the spot of X-rays, or the beam of X-rays. The only motion required is a smooth linear motion of the test object to be imaged. However, one skilled in the art will recognize that an equivalent system is one in which the test object to be imaged remains stationary and the X-ray detector(s), the X-ray tube(s) and the beam(s) of X-rays execute a smooth linear motion with respect to the stationary test object to be imaged, thereby generating shadowgraph images which may be added together to form laminographic cross sectional images of any preselected plane within the stationary test object as previously described. FIG. 8 shows an example of such an equivalent system wherein the test object to be imaged remains stationary and the X-ray tube(s) and X-ray detector(s) execute a smooth linear motion with respect to the stationary test object to be imaged. In FIG. 8, the same reference numerals are used for identical or corresponding elements of the embodiments shown in previous figures.

As shown in FIG. 8, the first X-ray source 10 and the second X-ray source 20 are mounted on an upper arm 602 of a C-shaped channel support unit 604 such that they are positioned above and along opposing sides of the circuit boards 120 which are arranged on a circuit board support unit 608. The circuit board support unit 608 has apertures 610 over which the circuit boards 120 are arranged so that the X-ray beams 130, 132, 134, 136 pass through the circuit boards 120 only, i.e., not through the circuit board support unit 608, in their paths from the X-ray sources 10, 20 to the X-ray detectors 40, 50, 60, 70. The first X-ray source 10 includes the front collimator 32 and the rear collimator 34. Similarly, the second X-ray source 20 includes the front collimator 36 and the rear collimator 38 (not shown in FIG. 8). The first, second, third and fourth linear X-ray detectors 40, 50, 60, 70 are mounted on a lower arm 606 of the C-shaped channel support unit 604. The first linear X-ray detector 40 is positioned adjacent to the second linear X-ray detector 50 to the right (positive X-direction) of a centerline (not shown) along the Y-direction defined by connecting the first X-ray source 10 with the second X-ray source 20. The third linear X-ray detector 60 is located adjacent to the fourth linear X-ray detector 70 to the left (negative X-direction) of the centerline connecting the first and second X-ray sources 10, 20. Each of the first, second, third and fourth linear X-ray detectors 40, 50, 60, 70 are thus located below the circuit boards 120; the circuit board support unit apertures 610; and the circuit board support unit lower arm 606. The C-shaped channel support unit 604 is mounted on slide rails 612 thereby allowing the C-shaped channel support unit 604, along with the attached first and second X-ray sources 10, 20 and the first, second, third and fourth linear X-ray detectors 40, 50, 60, 70, to move as a unit in the positive and negative X-directions. The synchronized drive motor 90 (FIG. 1) controls the motion of the C-shaped channel support unit 604 on the slide rails 612. As previously discussed, the synchronized drive motor 90 is connected to the control computer and image analysis system 100 (FIG. 1). The control computer and image analysis system 100 is also connected to the first, second, third and fourth linear X-ray detectors 40, 50, 60, 70.

In operation, the embodiment of FIG. 8 works in same way as the FIG. 1 embodiment previously described with the following exception. In the FIG. 1 embodiment, a linear scan of the circuit boards is performed by holding the first and second X-ray sources 10, 20 and the first, second, third and fourth linear X-ray detectors 40, 50, 60, 70 in a fixed or stationary position and moving the circuit boards 120a, 120b, 120c through the X-ray beams 130, 132, 134, 136 on the conveyor system 30. In the FIG. 8 embodiment, a linear scan of the circuit boards by the X-ray beams 130, 132, 134, 136 is performed by holding the circuit boards 120a, 120b, 120c in a fixed or stationary position on the circuit board support unit 608 and moving the C-shaped channel support unit 604 with the attached first and second X-ray sources 10, 20 and the first, second, third and fourth linear X-ray detectors 40, 50, 60, 70 past the circuit boards 120 via the slide rails 612. One skilled in the art will recognize that the linear scans thus produced by the embodiments of FIG. 1 and FIG. 8 are equivalent.

It will be understood that the apparatus and method of the present invention for continuous linear scan laminography may be embodied in other specific forms without departing from its spirit or essential characteristics. Thus, there are numerous other embodiments of the continuous linear scan laminography system and method which will be obvious to one skilled in the art. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

I claim:

1. An imaging system comprising:

a first X-ray source positioned on a first side of a longitudinal axis of the imaging system;

a first linear X-ray detector positioned to intercept X-rays emitted by said first X-ray source at a first angle;

a second linear X-ray detector positioned to intercept X-rays emitted by said first X-ray source at a second angle;

a second X-ray source laterally positioned with respect to said first X-ray source on a second side of said imaging system longitudinal axis opposite said first side of said imaging system longitudinal axis;

a third linear X-ray detector positioned to intercept X-rays emitted by said second X-ray source at a third angle;

a fourth linear X-ray detector positioned to intercept X-rays emitted by said second X-ray source at a fourth angle;

a linear motion system positioned between said first and second X-ray source, and said first, second, third and fourth linear X-ray detectors, said linear motion system further having a support for an object under test, said linear motion system configured to transport said object under test along said imaging system longitudinal axis through said X-rays emitted at said first angle and said second angle and detected by said first linear X-ray detector and said second linear X-ray detector, respectively, and through said X-rays emitted at said third angle and said fourth angle and detected by said third linear X-ray detector and said fourth linear X-ray detector, respectively, after having passed through said object under test, thereby forming first, second, third and fourth shadowgraph images of said object under test; and a control system connected to said linear motion system and said first, second, third and fourth linear X-ray detectors, wherein said control system regulates said linear motion system and the formation of said first, second, third and fourth shadowgraph images to produce a laminographic cross sectional image of a cutting plane of said object under test.

2. An imaging system as defined in claim 1 further comprising a first collimator positioned with respect to said first X-ray source such that said first collimator is configured to direct X-rays emitted by said first X-ray source toward said first linear X-ray detector and to block X-rays travelling in other directions.

3. An imaging system as defined in claim 2 further comprising a second collimator positioned with respect to said first X-ray source such that said second collimator is configured to direct X-rays emitted by said first X-ray source toward said second linear X-ray detector and to block X-rays travelling in other directions.

4. An imaging system as defined in claim 1 further comprising a third collimator positioned with respect to said second X-ray source such that said third collimator is configured to direct X-rays emitted by said second X-ray source toward said third linear X-ray detector and to block X-rays travelling in other directions.

5. An imaging system as defined in claim 4 further comprising a fourth collimator positioned with respect to said second X-ray source such that said fourth collimator is configured to direct X-rays emitted by said second X-ray source toward said fourth linear X-ray detector and to block X-rays travelling in other directions.

6. An imaging system as defined in claim 1 wherein said first, second, third and fourth linear X-ray detectors further comprise monolithic, self-scanning, linear, photodiode arrays.

7. An imaging system as defined in claim 6 further comprising an X-ray scintillation material deposited on said first, second, third and fourth linear photodiode array X-ray detectors.

8. An imaging system as defined in claim 7 wherein said X-ray scintillation material further comprises gadolinium oxysulfide.

9. An imaging system as defined in claim 1 wherein said linear motion system comprises a conveyor belt.

10. An apparatus for producing cross sectional images of a cutting plane within an object comprising:

a linear motion system having a longitudinal axis, said linear motion system adapted to support and transport an object under test along a substantially linear path;

a first source of X-rays for producing X-rays, said first source of X-rays positioned on a first side of said linear motion system longitudinal axis such that said X-rays produced by said first X-ray source impinge upon a first surface of said object and scan said object as said linear transport system moves said object along said linear path;

a first linear X-ray detector comprising a plurality of X-ray detector elements positioned adjacently in a substantially linear fashion, said first linear X-ray detector positioned adjacent a second surface of said object substantially opposite said first surface, said first linear X-ray detector thereby intercepting and detecting X-rays which enter said object through said first surface and exit said object through said second surface, said first linear X-ray detector positioned at a first angle with respect to said first source of X-rays;

a first linear X-ray detector readout control system, said first linear X-ray detector readout control system further having a clock which controls the periodic reading and storing of signals produced by said plurality of X-ray detector elements;

a second linear X-ray detector positioned a distance away from said first linear X-ray detector, said second linear X-ray detector comprising a plurality of X-ray detector elements positioned adjacently in a substantially linear fashion, said second linear X-ray detector positioned adjacent said second surface of said object substantially opposite said first surface, said second linear X-ray detector thereby intercepting and detecting X-rays which enter said object through said first surface and exit said object through said second surface, said second linear X-ray detector positioned at a second angle with respect to said first source of X-rays;

a second linear X-ray detector readout control system, said second linear X-ray detector readout control system further having a clock which controls the periodic reading and storing of signals produced by said plurality of X-ray detector elements;

a second source of X-rays laterally positioned with respect to said first source of X-rays on a second side of said linear motion system longitudinal axis opposite said first side of said linear motion system longitudinal axis;

a third linear X-ray detector positioned to intercept X-rays emitted by said second source of X-rays at a third angle, wherein said third linear X-ray detector comprises a plurality of X-ray detector elements positioned adjacently in a substantially linear fashion, said third linear X-ray detector positioned adjacent said second surface of said object substantially opposite said first surface, said third linear X-ray detector thereby intercepting and detecting X-rays which enter said object through said first surface and exit said object through said second surface, said third linear X-ray detector positioned at a third angle with respect to said second source of X-rays;

a third linear X-ray detector readout control system, said third linear X-ray detector readout control system further having a clock which controls the periodic reading and storing of signals produced by said plurality of X-ray detector elements;

a fourth linear X-ray detector positioned to intercept X-rays emitted by said second source of X-rays at a fourth angle, wherein said fourth linear X-ray detector comprises a plurality of X-ray detector elements positioned adjacently in a substantially linear fashion, said fourth linear X-ray detector positioned adjacent said second surface of said object substantially opposite said first surface, said fourth linear X-ray detector thereby intercepting and detecting X-rays which enter said object through said first surface and exit said object through said second surface, said fourth linear X-ray detector positioned at a fourth angle with respect to said second source of X-rays;

a fourth linear X-ray detector readout control system, said fourth linear X-ray detector readout control system further having a clock which controls the periodic reading and storing of signals produced by said plurality of X-ray detector elements;

a control system which controls and coordinates the operation of said linear motion system and said first, second, third and fourth linear X-ray detector readout control systems such that said first linear X-ray detector produces a first X-ray shadowgraph image of said object, said second linear X-ray detector produces a second X-ray shadowgraph image of said object, said third linear X-ray detector produces a third X-ray shadowgraph image of said object and said fourth linear X-ray detector produces a fourth X-ray shadowgraph image of said object; and an image analysis system which receives said first, second, third and fourth X-ray shadowgraph images of said object and combines said first, second, third and fourth X-ray shadowgraph images of said object to form a cross sectional image of a cutting plane of said object.

11. An apparatus as defined in claim 10 further comprising a first collimator positioned with respect to said first source of X-rays such that said first collimator is configured to direct X-rays emitted by said first source of X-rays toward said first linear X-ray detector and to block X-rays travelling in other directions.

12. An apparatus as defined in claim 11 further comprising a second collimator positioned with respect to said first source of X-rays such that said second collimator is configured to direct X-rays emitted by said first source of X-rays toward said second linear X-ray detector and to block X-rays travelling in other directions.

13. An apparatus as defined in claim 10 further comprising a third collimator positioned with respect to said second source of X-rays such that said third collimator is configured to direct X-rays emitted by said second source of X-rays toward said third linear X-ray detector and to block X-rays travelling in other directions.

14. An apparatus as defined in claim 13 further comprising a fourth collimator positioned with respect to said second source of X-rays such that said fourth collimator is configured to direct X-rays emitted by said second source of X-rays toward said fourth linear X-ray detector and to block X-rays travelling in other directions.

15. An apparatus as defined in claim 10 wherein said first, second, third and fourth linear X-ray detectors further comprise monolithic, self-scanning, linear, photodiode arrays.

16. An apparatus as defined in claim 15 further comprising an X-ray scintillation material deposited on said first, second, third and fourth linear photodiode array X-ray detectors.

17. An apparatus as defined in claim 16 wherein said X-ray scintillation material further comprises gadolinium oxysulfide.

18. An apparatus as defined in claim 10 wherein said linear motion system comprises a conveyor belt.

19. A method of producing a cross sectional image of an object comprising the steps of:

providing a first source of X-rays positioned on a first side of a linear motion system longitudinal axis;

detecting X-rays produced by said first source of X-rays with a first linear X-ray detector after said X-rays have impinged upon and penetrated said object from a first angular orientation;

detecting X-rays produced by said first source of X-rays with a second linear X-ray detector after said X-rays have impinged upon and penetrated said object from a second angular orientation;

providing a second source of X-rays laterally positioned with respect to said first source of X-rays on a second side of said linear motion system longitudinal axis;

detecting X-rays produced by said second source of X-rays with a third linear X-ray detector after said X-rays have impinged upon and penetrated said object from a third angular orientation;

detecting X-rays produced by said second source of X-rays with a fourth linear X-ray detector after said X-rays have impinged upon and penetrated said object from a fourth angular orientation;

moving said object between said first and second sources of X-rays and said first, second, third and fourth linear X-ray detectors along a substantially linear path which is substantially parallel to said linear motion system longitudinal axis;

producing a first X-ray shadowgraph image of said object with said X-rays detected by said first linear X-ray detector as said object traverses said substantially linear path between said first source of X-rays and said first linear X-ray detector;

producing a second X-ray shadowgraph image of said object with said X-rays detected by said second linear X-ray detector as said object traverses said substantially linear path between said first source of X-rays and said second linear X-ray detector;

producing a third X-ray shadowgraph image of said object with said X-rays detected by said third linear X-ray detector as said object traverses said substantially linear path between said second source of X-rays and said third linear X-ray detector;

producing a fourth X-ray shadowgraph image of said object with said X-rays detected by said fourth linear X-ray detector as said object traverses said substantially linear path between said second source of X-rays and said fourth linear X-ray detector; and combining said first, second, third and fourth X-ray shadowgraph images of said object to form a cross sectional image of said object.

20. A method as defined in claim 19 further comprising the step of collimating said first source of X-rays with a first collimator configured to direct X-rays emitted by said first source of X-rays toward said first linear X-ray detector and to block X-rays travelling in other directions.

21. A method as defined in claim 20 further comprising the step of collimating said first source of X-rays with a second collimator configured to direct X-rays emitted by said first source of X-rays toward said second linear X-ray detector and to block X-rays travelling in other directions.

22. A method as defined in claim 19 further comprising the step of collimating said second source of X-rays with a third collimator configured to direct X-rays emitted by said second source of X-rays toward said third linear X-ray detector and to block X-rays travelling in other directions.

23. A method as defined in claim 19 further comprising the step of collimating said second source of X-rays with a fourth collimator configured to direct X-rays emitted by said second source of X-rays toward said fourth linear X-ray detector and to block X-rays travelling in other directions.

24. A method as defined in claim 19 wherein said steps of detecting X-rays with said first, second, third and fourth linear X-ray detectors further comprise the step of providing monolithic, self-scanning, linear, photodiode arrays.

25. A method as defined in claim 24 further comprising the step of depositing an X-ray scintillation material on said first, second, third and fourth linear photodiode arrays.

26. A method as defined in claim 25 further comprising the step of selecting gadolinium oxysulfide as said X-ray scintillation material.

27. An imaging system comprising:

a first X-ray source positioned on a first side of a longitudinal axis of the imaging system;

a second X-ray source positioned on a second side of said longitudinal axis of the imaging system;

a first linear X-ray detector positioned to intercept X-rays emitted by said first X-ray source at a first angle;

a second linear X-ray detector positioned to intercept X-rays emitted by said first X-ray source at a second angle;

a third linear X-ray detector positioned to intercept X-rays emitted by said second X-ray source at a third angle;

a fourth linear X-ray detector positioned to intercept X-rays emitted by said second X-ray source at a fourth angle;

a linear motion system to which said first and second X-ray sources and said first, second, third and fourth linear X-ray detectors are mounted, said linear motion system further having a path for a stationary object under test to pass, said linear motion system configured to transport said first and second X-ray sources and said first, second, third and fourth linear X-ray detectors past said stationary object under test such that said X-rays emitted at said first, second, third and fourth angles and detected by said first, second, third and fourth linear X-ray detectors, respectively, after having passed through said stationary object under test, thereby form a first shadowgraph image, a second shadowgraph image, a third shadowgraph image and a fourth shadowgraph image of said stationary object under test; and a control system connected to said linear motion system and said first, second, third and fourth linear X-ray detectors, wherein said control system regulates said linear motion system and the formation of said first, second, third and fourth shadowgraph images to produce a laminographic cross sectional image of a cutting plane of said stationary object under test.

28. An imaging system as defined in claim 25 further comprising a first collimator positioned with respect to said first X-ray source such that said first collimator is configured to direct X-rays emitted by said first X-ray source toward said first linear X-ray detector and to block X-rays travelling in other directions.

29. An imaging system as defined in claim 28 further comprising a second collimator positioned with respect to said first X-ray source such that said second collimator is configured to direct X-rays emitted by said first X-ray source toward said second linear X-ray detector and to block X-rays travelling in other directions.

30. A method of producing a cross sectional image of a stationary object comprising the steps of:

providing a first source of X-rays positioned on a first side of a linear motion system longitudinal axis;

detecting X-rays produced by said first source of X-rays with a first linear X-ray detector after said X-rays have impinged upon and penetrated said stationary object from a first angular orientation;

detecting X-rays produced by said first source of X-rays with a second linear X-ray detector after said X-rays have impinged upon and penetrated said stationary object from a second angular orientation;

providing a second source of X-rays positioned on a second side of said linear motion system longitudinal axis;

detecting X-rays produced by said second source of X-rays with a third linear X-ray detector after said X-rays have impinged upon and penetrated said stationary object from a third angular orientation;

detecting X-rays produced by said second source of X-rays with a fourth linear X-ray detector after said X-rays have impinged upon and penetrated said stationary object from a fourth angular orientation;

moving said first and second source of X-rays and said first, second, third and fourth linear X-ray detectors along a substantially linear path past said stationary object such that said X-rays from said first and second sources of X-rays penetrate said stationary object and are detected by said first, second, third and fourth linear X-ray detectors;

producing a first X-ray shadowgraph image of said stationary object with said X-rays detected by said first linear X-ray detector as said first linear X-ray detector and said first source of X-rays traverse said substantially linear path past said stationary object;

producing a second X-ray shadowgraph image of said stationary object with said X-rays detected by said second linear X-ray detector as said second linear X-ray detector and said first source of X-rays traverse said substantially linear path past said stationary object;

producing a third X-ray shadowgraph image of said stationary object with said X-rays detected by said third linear X-ray detector as said third linear X-ray detector and said second source of X-rays traverse said substantially linear path past said stationary object;

producing a fourth X-ray shadowgraph image of said stationary object with said X-rays detected by said fourth linear X-ray detector as said fourth linear X-ray detector and said second source of X-rays traverse said substantially linear path past said stationary object; and combining said first, second, third and fourth X-ray shadowgraph images of said stationary object to form a cross sectional image of said stationary object.

31. A method as defined in claim 30 further comprising the step of collimating said first source of X-rays with a first collimator configured to direct X-rays emitted by said first source of X-rays toward said first linear X-ray detector and to block X-rays travelling in other directions.

32. A method as defined in claim 31 further comprising the step of collimating said first source of X-rays with a second collimator configured to direct X-rays emitted by said first source of X-rays toward said second linear X-ray detector and to block X-rays travelling in other directions.

33. A method as defined in claim 30 further comprising the step of collimating said second source of X-rays with a third collimator configured to direct X-rays emitted by said second source of X-rays toward said third linear X-ray detector and to block X-rays travelling in other directions.

34. A method as defined in claim 33 further comprising the step of collimating said second source of X-rays with a fourth collimator configured to direct X-rays emitted by said second source of X-rays toward said fourth linear X-ray detector and to block X-rays travelling in other directions.

* * * * *

UNITED STATES PATENT AND TRADEMARK OFFICE
CERTIFICATE OF CORRECTION

PATENT NO.   : 5,583,904
DATED        : December 10, 1996
INVENTOR(S)  : John A. Adams It is certified that error appears in the above-identified patent and that said Letters Patent is hereby corrected as shown below:

Column 16
Line 25, delete "source" and insert therefore -- sources --

Column 21
Line 8, delete "25" and insert therefore -- 27 --

Signed and Sealed this

Twenty-fifth Day of March, 2003

JAMES E. ROGAN
*Director of the United States Patent and Trademark Office*